United States Patent
Svensson et al.

(10) Patent No.: US 8,117,901 B2
(45) Date of Patent: Feb. 21, 2012

(54) DETERMINATION OF SLURRY CONCENTRATION

(75) Inventors: Joakim Svensson, Uppsala (SE); Hanno Ehring, Uppsala (SE); Esfir Lofman, Uppsala (SE); Lars Andersson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 698 days.

(21) Appl. No.: 12/147,591

(22) Filed: Jun. 27, 2008

(65) Prior Publication Data

US 2009/0007643 A1    Jan. 8, 2009

(30) Foreign Application Priority Data

Jul. 6, 2007 (SE) ....................... 0701671

(51) Int. Cl.
*G01N 30/02* (2006.01)
(52) U.S. Cl. ............. 73/61.53; 73/61.43; 73/61.41; 73/53.01
(58) Field of Classification Search ............ 73/61.53, 73/61.43, 61.41, 53.01
See application file for complete search history.

(56) References Cited

U.S. PATENT DOCUMENTS

| | | | | |
|---|---|---|---|---|
| 2003/0089662 | A1* | 5/2003 | Hofmann | 210/656 |
| 2007/0012626 | A1* | 1/2007 | Andersson et al. | 210/656 |
| 2007/0090053 | A1* | 4/2007 | Windahl | 210/656 |

FOREIGN PATENT DOCUMENTS

| GB | 2 394 191 | 4/2004 |
|---|---|---|
| WO | WO 2006/122824 | 11/2006 |

* cited by examiner

*Primary Examiner* — Hezron E Williams
*Assistant Examiner* — Rodney T Frank

(57) ABSTRACT

A method for determining the concentration of a chromatographic medium in a liquid slurry comprises the steps of: providing a column (1) having a top end (3) and a bottom end (2) and adapted to retain a chromatographic medium therein; introducing a defined volume of the slurry (15) into the column (1); providing a liquid flow through the column (1) from the top end to the bottom end of the column to settle the chromatographic medium in the column; measuring the bed height of the consolidated chromatographic medium or a value related thereto; and determining from the measured bed height or value related thereto the concentration, or a value related to the concentration of the chromatographic medium in the slurry. A device for performing the method as well as the use of the method in packing of especially large scale columns are also disclosed.

10 Claims, 8 Drawing Sheets

DETERMINATION OF SLURRY CONCENTRATION

CROSS-REFERENCE TO RELATED APPLICATIONS

This application claims priority to Swedish patent application number 0701671-0 filed on Jul. 6, 2007; the disclosure of which is incorporated herein by reference in its entirety.

TECHNICAL FIELD

The present application relates to a method and a device for determining the concentration of a chromatographic medium in a liquid slurry or suspension as well as to use of the method in chromatography column packing.

BACKGROUND OF THE INVENTION

Chromatography is a well-established and valuable technique in both preparative and analytical work as well as in purification generally. Typical industrial chromatography apparatus has an upright housing, or column, in which a bed of packing material, usually a particulate medium, rests against a permeable retaining layer. Fluid mobile phase enters through an inlet e.g. at the top of the column, usually through a porous, perforated, mesh or other restricted-permeability layer, moves through the packed bed and is taken out at an outlet, typically below a restricted-permeability layer.

The bed of packing material is usually filled in the column by applying a defined amount of a slurry of the medium to the column and settling the medium in the column by a liquid flow through the column. Knowledge of slurry concentration is very vital when packing columns at any scale but foremost at pilot to process scale so that the correct amount of media can be transferred to the column. This is necessary to achieve the correct bed height at the correct compression in a reproducible manner. This is currently one of the most poorly controlled aspects of column packing and causes many failed attempts.

Today, slurry concentration is often measured by gravity settling in a graduated cylinder overnight. This requires planning and accuracy, which is often lacking. In addition, many media do not settle fully after overnight settling which is standard but requires longer time. This is often neglected and the measured slurry concentration often deviates much from the correct value. The use of different buffers can also cause the medium to settle differently.

There is therefore a need for means which may simplify the concentration determination as well as increase the determination quality which introduces less variation in the process by varying bed compression, bed height or both.

SUMMARY OF THE INVENTION

One object of the invention is to provide an improved method for determining slurry concentration. This is achieved with a method according to claim 1. With this method it is possible to measure slurry concentrations accurately within a short time, e.g. within 1 hour. The general applicability of the method makes it suitable for all types of chromatography media.

Another object of the invention is to provide an improved method of column packing. This is achieved with a method according to claim 8 and comprises the use in column packing of the above-mentioned method for determining slurry concentration.

Still another object of the invention is to provide a device for determining slurry concentration. This is achieved with a device according to claim 11. This device may be made simple, and may optionally be of disposable type.

In a preferred embodiment of the method for determining slurry concentration, the method includes a step of washing the volume of slurried medium used for concentration determination before the concentration is measured.

Further suitable embodiments are described in the dependent claims.

In the following, the invention will be described in more detail, by way of example only and not limitation, by the following description where reference is made to the accompanying drawings.

DETAILED DESCRIPTION OF THE INVENTION

As mentioned above, the present invention provides a method and device for measuring the concentration of a chromatographic medium in a liquid slurry (suspension). Knowledge of the slurry concentration then makes it possible to use the slurry to pack especially a large scale column with the correct amount of media to obtain the correct bed height at the correct compression. In brief, the method comprises settling the slurry in a column by using a flow (i.e. similar to the media packing in the large scale column, but not necessarily with the same flow rate), and then measuring the height of the consolidated medium to obtain the slurry concentration, or a value or measure related to the slurry concentration. While the method of the invention may be used in connection with packing of columns at any scale, it is contemplated to be of most benefit to packing columns in the pilot to process scale. An embodiment of the device will now be described with reference to FIGS. 1 to 6. Corresponding parts have the same reference designations throughout the Figures. Suitably a level measuring device is provided to the column in order to be able to automatically measure both the level of the initially introduced slurry and the final level of the settled bed. This will be described in relation to FIGS. 7 and 8.

Figure 1:
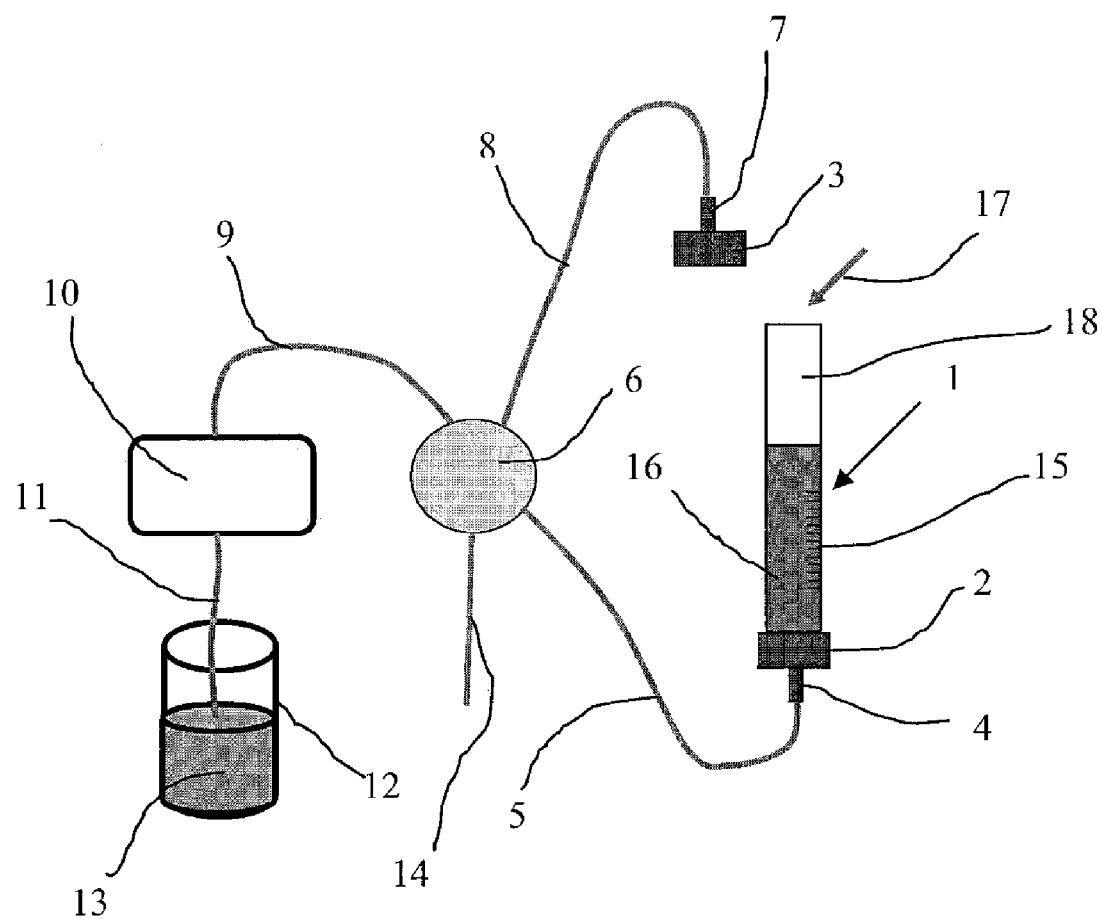
FIG. 1 is a schematic view of a device according to the present invention for determining slurry concentration where the column has been filled with a defined volume of a slurry whose concentration is to be determined.

The device illustrated in FIGS. 1 to 6 comprises a chromatographic column 1 having end pieces in the form of a bottom cap 2 and a top cap 3 which both include filters or the like to retain a chromatographic medium in the column (in FIG. 1, the top cap 3 is removed from the column top end). The chromatographic column 1 is preferably mounted vertically to give an even surface. This is suitable when the surface level should be measured. The bottom cap 2 has an inlet/outlet 4 which via a conduit 5 is connected to a selector valve 6. Similarly, the top cap 3 has an inlet/outlet 7 which via a conduit 8 is connected to the valve 6. Valve 6 is also via a conduit 9 connected to a pump 10 which in turn via a conduit 11 is connected to a vessel 12 with liquid (buffer) 13, e.g. water. The liquid 13 is preferably the same as, or at least representative for the liquid that will be used for packing the large scale column, (often, the slurry is in a storage solution, e.g. 20% ethanol, which will be replaced when packing the large scale column). A conduit 14 connects pump 10 via selector valve 6 to waste (not shown). Column 1 is in the illustrated case provided with a scale 15 (may, however, be replaced by other means, such as a transparent ruler or the like. Other suitable level measuring means will be described in relation to FIGS. 7 and 8). Measurement of the slurry concentration in column 1 may be performed as follows.

Figure 2:
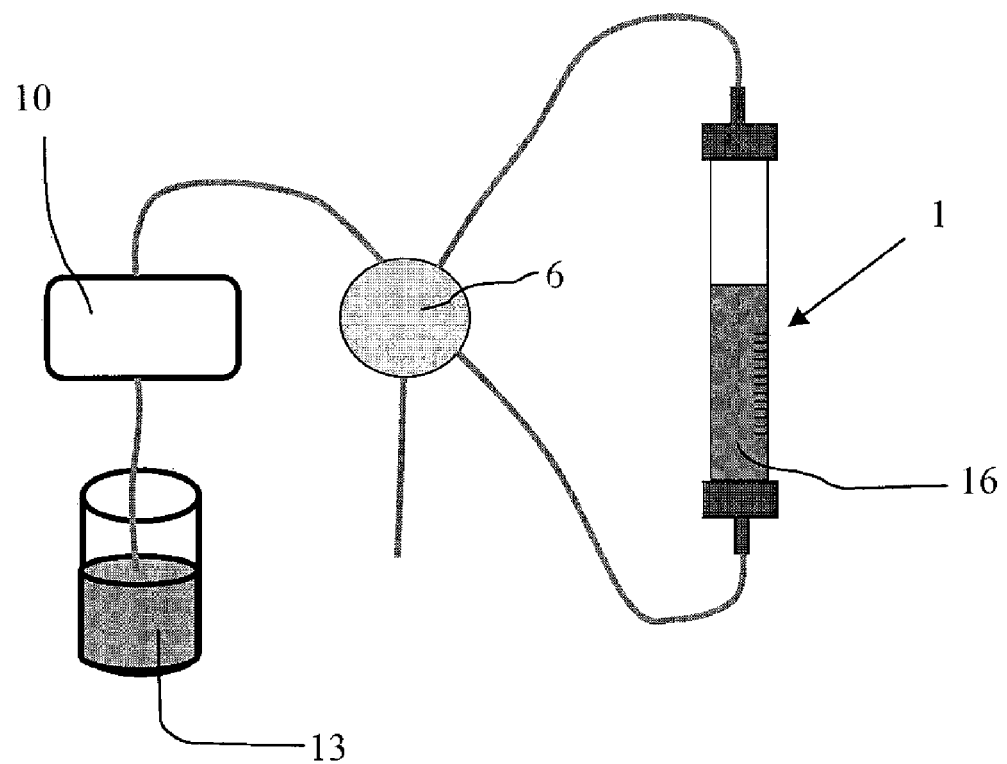
FIG. 2 is a similar view to FIG. 1 where the column top end has been closed by a cap.

With reference first to FIG. 1, with the top cap 3 removed from the column top, a volume of a slurry 16 for which the concentration (or a concentration related value) is to be measured is filled into the column 1 through the open column top as indicated by arrow 17, e.g. added up to a predetermined level, e.g. 100 mm height. Alternatively any volume of the slurry is filled into the column and an automatic level measuring device is used for measuring the filling height and therefore the volume. When the column is not completely filled with slurry 16, water 18 is added to completely fill the column. The top cap 3 is then mounted on the column top as shown in FIG. 2.

Figure 3:
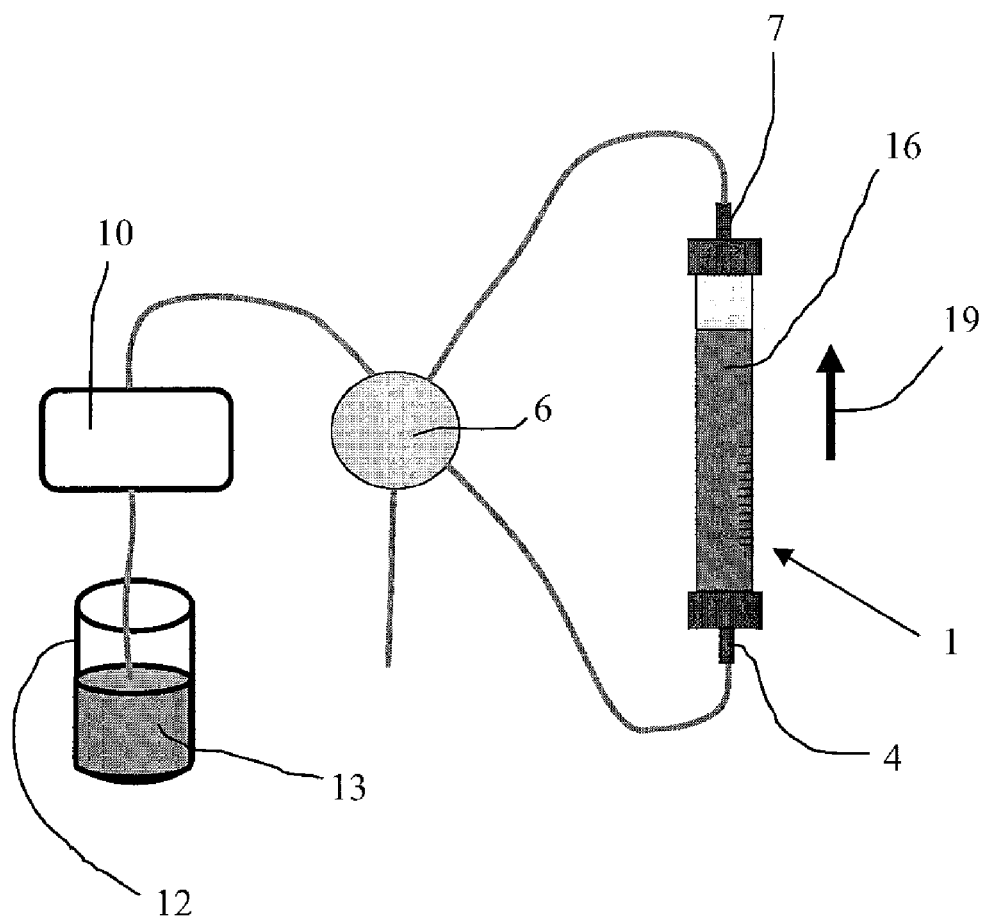
FIG. 3 is a similar view to FIG. 2 where wash of the slurry has been initiated with a counter flow of liquid from the bottom to the top of the column.
Figure 4:
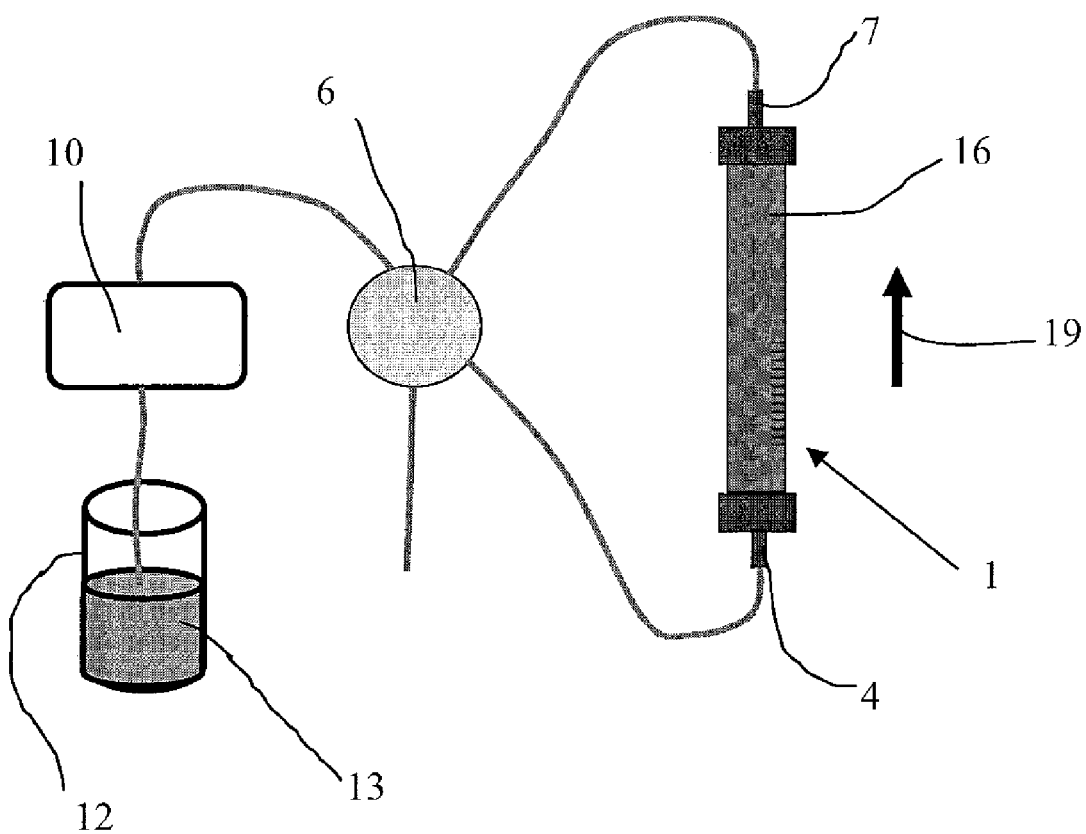
FIG. 4 is a similar view to FIG. 3 where wash liquid with mixed medium therein extends to the top of the column (and the medium starts packing towards the top).
Figure 5:
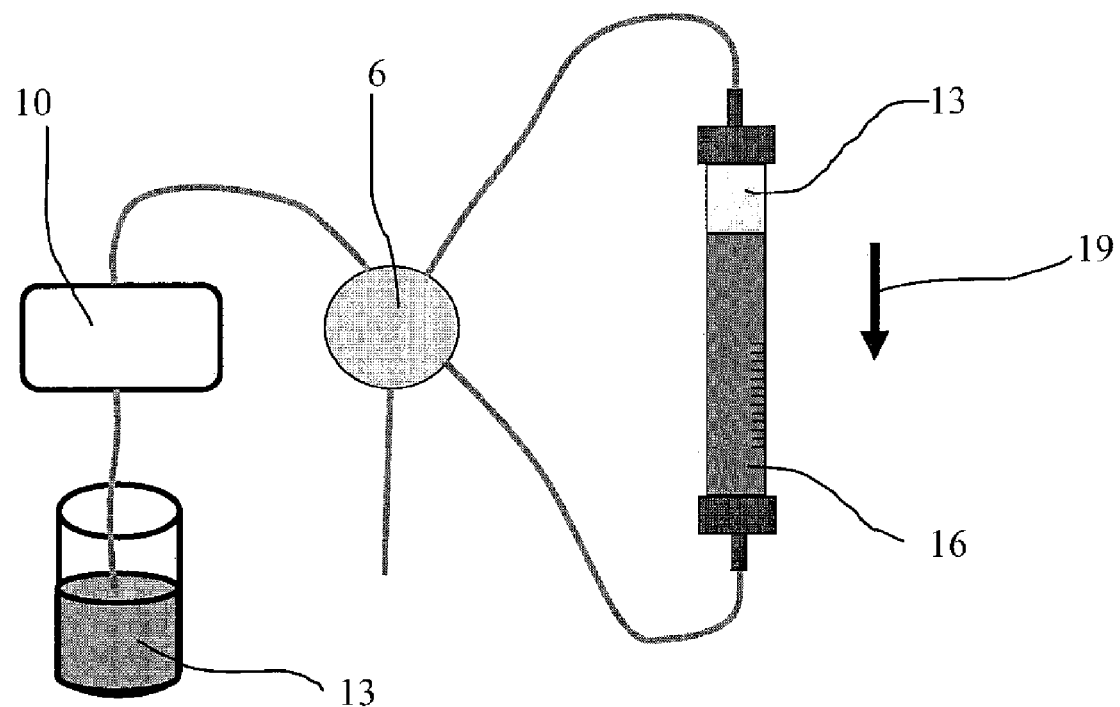
FIG. 5 is a similar view to FIGS. 3 and 4 where the media consolidation has been started by introducing a liquid flow from the top to the bottom of the column.

Referring now to FIG. 3, selector valve 6 is set to connect pump 10 to the column bottom inlet 4, and the column outlet 7 to waste, and the pump is actuated to run a flow of wash buffer 13 from vessel 12 through the column 1 in the direction from the bottom to the top of the column as indicated by arrow 19. In this process, the media will be mixed to some degree with liquid throughout the column volume as shown in FIG. 4. (Actually, in practice, the mixing will not be throughout the whole column as shown in FIG. 4 but the lower part of the column will rather be filled with buffer and the media will be lifted to the top of the column by the flow.) After an appropriate amount of wash liquid has passed through the column, e.g. five column volumes, the slurry 16 is washed free of storage solution. An alternative to this reverse flow procedure would be to settle the media at the bottom of the column by pumping liquid from the top to the bottom. Then the top cap is removed and the settled media is manually stirred by some suitable stirring device until fully homogeneous. The top cap is thereafter replaced and the procedure is commenced.

Figure 6:
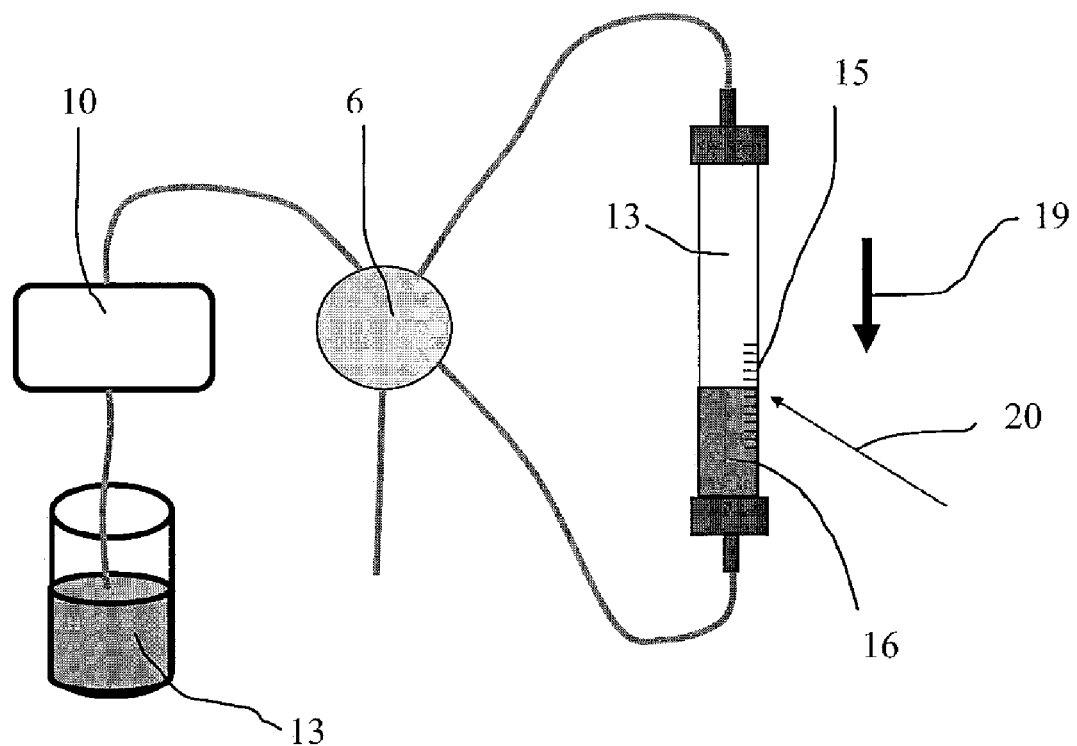
FIG. 6 is a similar view to FIG. 5 where the packing is completed and the bed height/slurry concentration can be read on the column.

The liquid flow through the column bottom inlet 4 is then stopped, and the valve 6 is set to connect pump 10 to the top inlet 7 of the column, and the bottom inlet 4 to waste. Optionally, the contents in the column is now mixed or re-suspended manually (after removing the top cap 3). The pump 10 is then actuated to pump buffer 13 from vessel 12 through the top inlet 7 to cause a downward flow through the column 1, as indicated by arrow 19 in FIG. 5. The flow through the column is continued until the media has been settled in the lower part of the column and the liquid 13 over the consolidated media bed is free from visible media particles, as indicated in FIG. 6. When the flow has been stopped, the media bed is allowed to stabilize for some time, say e.g. 30 minutes. Then the value for the top level of the media bed is read on the scale 15 on column 1, as indicated in FIG. 6 by arrow 20. This can be done either manually or automatically using some kind of level measuring device as will be described in relation to FIGS. 7 and 8. As mentioned above, this value may be the bed height or a value related thereto. This value may then be used to calculate the amount of slurry that is to be added to the large scale column to obtain the correct bed height and bed compression. Suitably, a table, diagram, graph or similar is provided from which the slurry amount may be read for different values read on the scale, and preferably also for different chromatographic media.

Optimal flow rates and times for washing and settling (consolidating) the media may vary depending on the particular media used. Such optimization may, however, readily be done by a person skilled in the art.

Optionally, the direction of the flow may be reversed one or more times (pulsating flow) during the wash procedure.

For high slurry concentrations (e.g. above 60% by volume), problems may arise due to less dense settling of media. This can easily be corrected by adding a defined volume of liquid, e.g. water, in the column before adding slurry to the predefined level and performing a simple calculation.

It is readily seen that the above described method and device may conveniently be automated.

Figure 7:
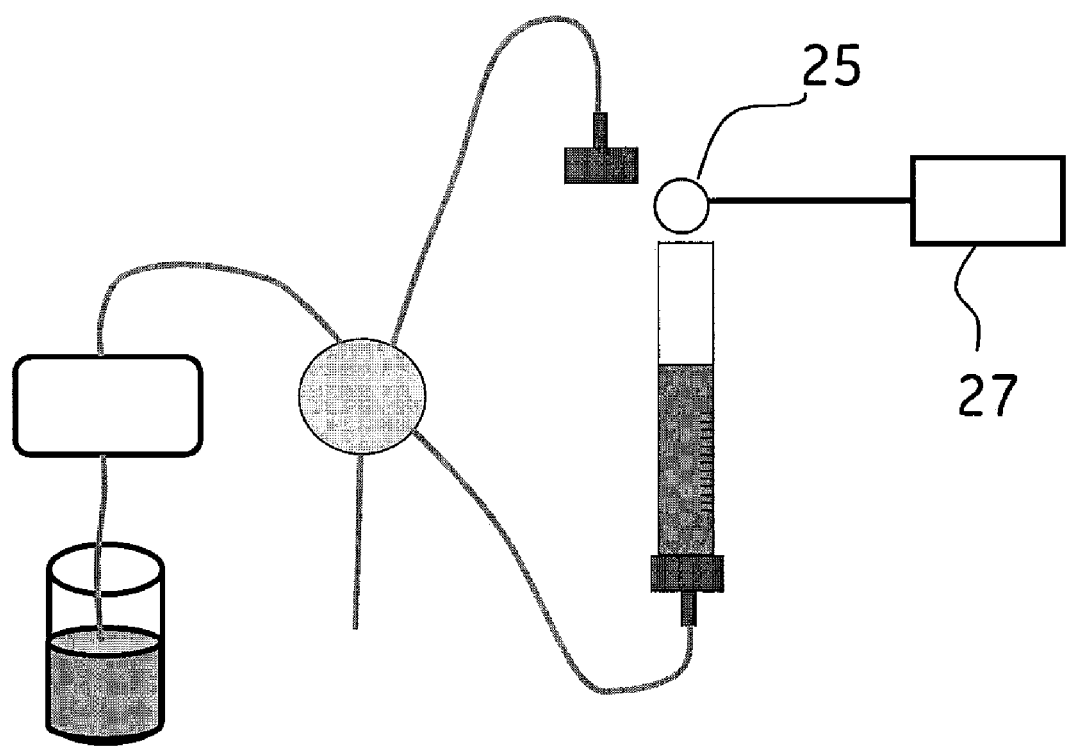
FIG. 7 is a similar view to FIG. 1 but including a level measuring device.

FIG. 7 shows schematically how a level measuring device 25 can be provided. In this example the level measuring device 25 is an ultrasound transducer. Hereby the level in the column can be measured. First the filling level of slurry is measured and from this measure a volume of filled slurry can be calculated and then at the end of the process (corresponding to FIG. 6) the level of the settled media bed is measured. From these measurements the initial slurry concentration can then be calculated. The level measuring device 25 is shown to be connected to a controlling and calculating device 27.

Figure 8:
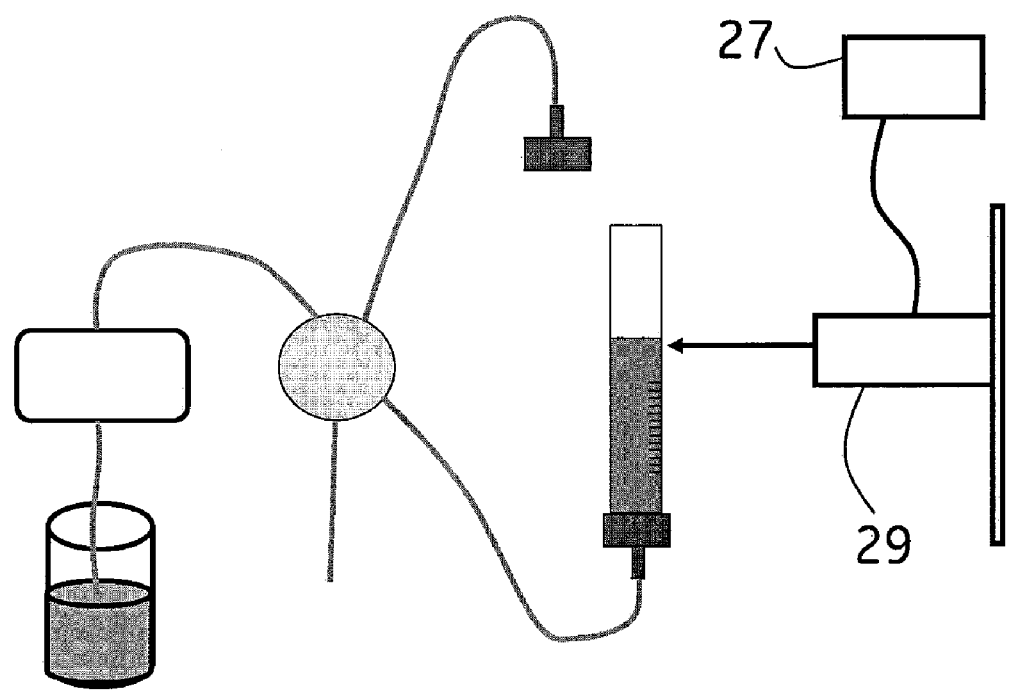
FIG. 8 is a similar view to FIG. 7 but including another type of level measuring device.

FIG. 8 is similar to FIG. 7 but shows another type of level measuring device 29. Here a light beam is used for detecting the level. Suitably the light beam transmitting device 29 is movably mounted on a rod such that the light beam can be moved along the height of the column to detect where the level is. Also here the light beam transmitting device 29 is connected to a controlling and calculating device 27.

To provide a further automated system a controlling device could be provided where the pump, the valve and the level measuring device are connected. Hereby this controlling device can determine at which flow and for how long the valve should be in a specific position for a specific medium. In this way it would be possible to only input to the controlling device which type of medium it is then the controlling device can control the whole process. Also the initial filling of slurry into the column could be controlled by this controlling device if the slurry is connected to the pump via a tube.

In the following specific Example, an embodiment of the method of the present invention is described which, while it may be used with the device described above and shown in FIGS. 1 to 6, uses a syringe instead of a pump, valve and associated conduits.

EXAMPLES

The present examples are provided for illustrative purposes only, and should not be construed as limiting the scope of the present invention as defined by the appended claims. All references given below and elsewhere in the present specification are hereby included herein by reference.

Measuring Slurry Concentration

This method is performed with a TRICORN™ 10 column. A syringe is used in the method described below but a pump can also be used. Slurry is added to the column then washed, re-suspended and allowed to settle for 30 min before the concentration is measured. The method is accurate for slurry concentrations below 60% (vol.). For higher concentrations, dilute the slurry by adding exactly 2 ml of water to the TRI-CORN™ column before adding the medium in step 5. Calculate the concentration in the barrel or tank (from which the slurry sample volume is taken) by dividing the measured concentration by the dilution factor 0.8.

Column Filling
1. Mount the bottom end piece with a filter on the TRI-CORN™10 column.
2. Carefully tape a transparent ruler on the side of the column, so that the zero point on the ruler coincides with the surface of the bottom filter.
3. Place a stopper in the bottom outlet.
4. Place the column in an upright position—preferably vertically perfect.
5. Add thoroughly mixed slurry to the column with a Pasteur pipette below the 10 cm mark to avoid medium on the column wall. Fill until 10 cm is reached.
6. Add water until the glass body of the column is filled.
7. Mount an end piece with filter on the top of the column.

Washing Step
1. Mount a 20 ml syringe filled with distilled water to the top of the column.
2. Remove the stopper from the bottom outlet of the column.
3. Wash by pressing the syringe at an approximate flow of 6-10 ml/min.
4. Wash with a total of 50-60 ml distilled water and avoid pressing air into the column.
5. Replace the stopper.

Re-Suspend and Settle
1. Remove the upper end piece.
2. Mix the medium in the column thoroughly by stirring with an appropriate tool.
3. Replace the upper end piece. Avoid air.
4. Mount a 20 ml syringe filled with distilled water to the upper end piece.
5. Remove the stopper from the bottom outlet of the column.
6. Press the syringe at 6-10 ml/min until the liquid over the media bed is free from particles.
7. Stop the flow.
8. Replace the stopper.

Determination of the Slurry Concentration
1. Allow the bed to stabilize for 30 min without flow.
2. Read the bed height.

The height after 30 min corresponds to the concentration of the slurry in the sample.

The method has been validated for CAPTO™ S (GE Healthcare Life Sciences, Uppsala, Sweden), a media which settles very loosely in its storage solution; for example, the same media volume gives 59% (vol.) in storage solution and 53% (vol.) in water. If this media is not washed completely free from its storage buffer, the concentration measurement will be very erroneous. Any conductivity in the buffer leads to these effects.

From the foregoing, it will be appreciated that, although specific embodiments of this invention have been described herein for purposes of illustration, various modifications may be made without departing from the spirit and scope of the invention. Accordingly, the invention is not limited except by the appended claims.

What is claimed is:

1. A method of determining the concentration of a chromatographic medium in a liquid slurry, comprising:
providing a column (1) having a top end (3) and a bottom end (2) and adapted to retain a chromatographic medium therein;
introducing a defined volume of the slurry (15) into the column (1);
providing a liquid flow through the column (1) from the top end to the bottom end of the column to settle the chromatographic medium in the column;
measuring the bed height of the consolidated chromatographic medium or a value related thereto; and
determining from the measured bed height or value related thereto the concentration, or a value related to the concentration of the chromatographic medium in the slurry;
wherein prior to settling the chromatographic medium, the medium is subjected to a wash step in the column (1).

2. The method of claim 1, further comprising measuring the introduced volume of the slurry automatically with a level measuring device (25; 29) and measuring the bed height of the consolidated chromatographic medium automatically with the level measuring device (25; 29).

3. The method of claim 1, wherein the wash step comprises flowing a liquid through the column (1) from the bottom end (2) towards the top end (3) of the column.

4. The method of claim 1, wherein the wash step comprises flowing a liquid through the column (1) from the top end (3) towards the bottom end (2) of the column (1), and mixing the medium in the column before settling the medium in the column.

5. The method of claim 1, wherein the wash step comprises flowing a liquid through the column (1) alternatingly from the bottom end (2) towards the top end (3), and from the top end (3) towards the bottom end (2) of the column.

6. The method of claim 1, wherein the liquid in the wash step is other than the liquid of the slurry.

7. The method of claim 1, wherein the settled medium is allowed to stabilize for a defined time before measuring the bed height or a value related thereto.

8. A method of packing a first column with a slurry of a chromatographic medium to obtain a desired bed height of packed medium in the column, comprising:
determining the concentration, or a value related the concentration, of the chromatographic medium in the slurry by the method of claim 1 using a second column (1);
determining from the determined slurry concentration or value related thereto the amount of slurry to be introduced into the first column to obtain the desired bed height therein; and
filling the first column with the determined slurry amount.

9. The method of claim 8, wherein the second column (1) is substantially smaller than the first column.

10. The method of claim 8, wherein the first column is a pilot type column or a process type column, and the second column (1) is a laboratory type column.

* * * * *